United States Patent [19]

Miyano et al.

[11] Patent Number: 4,564,624
[45] Date of Patent: Jan. 14, 1986

[54] 8-(SUBSTITUTED N-PHENYLCARBOXAMIDOMETHYL) PYRROLIZIDINES AND USE THEREOF AS ANTIARRHYTHMICS

[75] Inventors: Seiji Miyano, Fukuoka; Kunihiro Sumoto, Ohnojo; Minoru Morita, Minoo; Fumio Sato, Nagaokakyo, all of Japan

[73] Assignee: Suntory Ltd., Osaka, Japan

[21] Appl. No.: 473,947

[22] Filed: Mar. 10, 1983

[30] Foreign Application Priority Data

Mar. 16, 1982 [JP] Japan ................................. 57-42297

[51] Int. Cl.[4] ...................... A61K 31/40; C07D 487/04
[52] U.S. Cl. ........................................ 514/413; 548/453
[58] Field of Search ........................... 548/453; 514/413

Primary Examiner—Glennon H. Hollrah
Assistant Examiner—D. B. Springer
Attorney, Agent, or Firm—Burgess, Ryan & Wayne

[57] ABSTRACT

An 8-substituted pyrrolizidine derivative representable by the formula:

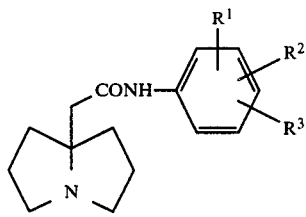

(wherein $R^1$ stands for hydrogen or a lower alkyl group, $R^2$ stands for hydrogen, a lower alkyl group, a lower alkoxy group or halogen, and $R^3$ stand for a lower alkyl group, a lower alkoxy group, amino group or halogen), which can be produced by reacting a corresponding substituted anilin with 8-halocarbonylmethyl pyrrolizidine or reacting an alkali metal salt of the corresponding substituted anilin with 8-alcoxycarbonylmethyl pyrrolizidine. The derivative is useful as an antiarrhythmic agent.

8 Claims, No Drawings

8-(SUBSTITUTED N-PHENYLCARBOXAMIDOMETHYL) PYRROLIZIDINES AND USE THEREOF AS ANTIARRHYTHMICS

This invention relates to novel 8-substituted pyrrolizidine derivatives and the use thereof.

Since we previously produced pyrrolizidine derivatives having a variety of substituents at 8 position (ref. to U.S. patent application Ser. No. 258,479 now abandoned), a further successive research has been carried out, which led us to this invention.

This invention is directed to a novel 8-substituted pyrrolizidine derivatives representable by the following formula:

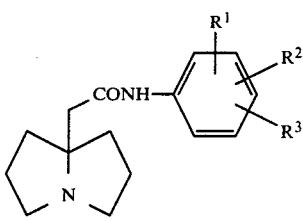

wherein $R^1$ stands for hydrogen or a lower alkyl group, $R^2$ stands for hydrogen, a lower alkyl group, a lower alkoxy group or halogen, and $R^3$ stands for a lower alkyl group, a lower alkoxy group, amino group or halogen, and to an antiarrhythmic agent composed of a derivative as above.

The compound (I) can be prepared, as shown by the following scheme, from 8-alkoxycarbonyl methyl pyrrolizidine (II), which is obtained by subjecting 8-cyanomethyl pyrrolizidine to alcoholysis in accordance with the description in the specification of the abovementioned U.S. application, and a corresponding substituted aniline derivative, the methods being as follows:

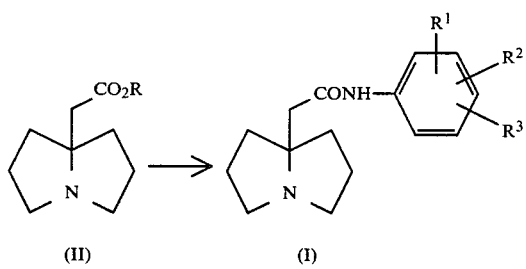

wherein R stands for methyl or ethyl group, and $R^1$, $R^2$, and $R^3$ are of the same meaning as defined above.

METHOD A

A compound of the formula (I) is prepared by subjecting 8-alkoxycarbonyl methyl pyrrolizidine (II) to hydrolysis with a mineral acid e.g. hydrochloric acid to give free carboxylic acid, on which is allowed a halogenating agent e.g. thionyl chloride to act to give an acid halogenide, which is allowed to react with a corresponding substituted aniline. The reaction is preferably conducted in a solvent which is capable of dissolving the acid halogenide but does not impede the reaction, the solvent being exemplified as chloroform. The reaction may be promoted by adding to the reaction system an inorganic base such as alkali hydroxide or an organic base such as triethylamine or pyridine, but the reaction proceeds even when no base is added.

METHOD B

A compound of the formula (I) is also producible by allowing 8-alkoxycarbonyl methyl pyrrolizidine (II) to react with an alkali metal salt of corresponding substituted aniline. The alkali metal salt can be formed by allowing an alkali metal compound such as sodium hydride, sodium amide or butyl lithium to act on a substituted aniline in an anhydrous solvent such as ether, tetrahydrofuran, dioxane or benzene.

In the above methods A and B, use of, as the substituted aniline, lower alkyl aniline, lower alkoxy aniline, halogenoaniline or amino aniline gives respectively corresponding 8-(substituted anilino)carbonyl methyl pyrrolizidine.

Thus obtained N-(substituted phenyl)-8-pyrrolizidineacetamide derivatives are novel compounds and have antiarrhythmic activity as described below.

ANTIARRHYTHMIC ACTIVITY

In accordance with the manner described by J. W. Lawson (Journal of Pharmacology and Experimental Therapeutics, Vol. 160, p. 22, 1968), ddY-strain male mice, each weighing 16–30 g. were treated with chloroform to induce ventricular arrhythmias. At the time when they ceased to breathe, electrocardiogram of each animal was recorded to observe the flutter and fibrillation of the ventricle.

The abnormalities of ventriculus as observed in these animals can be prevented by previous administration of a substance showing antiarrhythmic activity. A compound of this invention, at various dosages, was subcutaneously injected to mice grouped by 29–40 heads. Thirty minutes later these mice were treated with chloroform to induce arrhythmias. Prophylaxis percentages of the flutter and fibrillation of ventricle for each dosage were calculated. 50% Effective dosage ($ED_{50}$) and 95% confidence limit of each value thus found were calculated by the method of Litchfield and Wilcoxon (Journal of Pharmacology and Experimental therapeutics, Vol. 96, p. 99, 1949) as shown in Table I. 50% Lethal ($LD_{50}$) was calculated using ddY strain male mice, each weighing 18–22 g., by the "upp and down method" (Pharmacological Experiment, compiled by Takagi & Ozawa, p. 204, Nanzando, 1972), and the ratios of $LD_{50}$ and $ED_{50}$ are shown as well in Table I as "therapeutic index".

TABLE (I)

Antiarrhythmic Activity

| Compound No. | R | $ED_{50}$ mg/Kg (95% confidence limit) | $LD_{50}$ mg/Kg | Therapeutic index |
|---|---|---|---|---|
| 1 | $CH_3$— | >100  100 ($ED_{40}$) | 385 | |

TABLE (I)-continued

Antiarrhythmic Activity

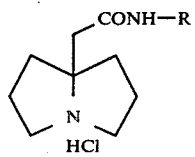
·HCl

| Compound No. | R | ED$_{50}$ mg/Kg (95% confidence limit) | LD$_{50}$ mg/Kg | Therapeutic index |
|---|---|---|---|---|
| 2 | –⟨⟩–CH$_3$ | n.e. (100) 100 (ED$_{20}$) | 413 | |
| 3 | 2-Cl-C$_6$H$_4$– | >100 100 (ED$_{20}$) | 347 | |
| 4 | 2-Br-C$_6$H$_4$– | 59 (38.1–91.5) | 445 | 7.54 |
| 5 | 2-CH$_3$O-C$_6$H$_4$– | >100 100 (ED$_{40}$) | 381 | |
| 6 | 3-OCH$_3$-C$_6$H$_4$– | >100 100 (ED$_{40}$) | 417 | |
| 7 | 4-OCH$_3$-C$_6$H$_4$– | 60 (21.7–100.2) | 288 | 4.80 |
| 8 | 2-H$_2$N-C$_6$H$_4$– | 100 (58.5–171) | 633 | 6.33 |
| 9 | 2,3-(CH$_3$)$_2$-C$_6$H$_3$– | 64 (40.8–103.5) | 469 | 7.33 |
| 10 | 3,4-(CH$_3$)$_2$-C$_6$H$_3$– | >100 100 (ED$_{40}$) | 398 | |
| 11 | 3,5-(CH$_3$)$_2$-C$_6$H$_3$– | 72 (41.1–126) | 400 | 5.56 |
| 12 | 2,3-(CH$_3$)$_2$-C$_6$H$_3$– | 24 (14–51) | 410 | 17.08 |
| 13 | 2,6-(CH$_3$)$_2$-C$_6$H$_3$– | 76 (59.4–97.3) | 559 | 7.36 |

TABLE (I)-continued

Antiarrhythmic Activity

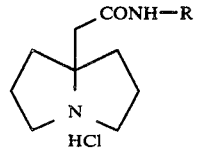
·HCl

| Compound No. | R | ED$_{50}$ mg/Kg (95% confidence limit) | LD$_{50}$ mg/Kg | Therapeutic index |
|---|---|---|---|---|
| 14 | 2,4-(CH$_3$)$_2$-C$_6$H$_3$– | 52 (34.9–77.5) | 355 | 6.83 |
| 15 | 2,4-(CH$_3$O)$_2$-C$_6$H$_3$– | 90 (71.4–113.4) | 203 | 2.26 |
| 16 | 2,6-Cl$_2$-C$_6$H$_3$– | >100 100 (ED$_{20}$) | 200 | |
| 17 | 2,6-(C$_2$H$_5$)$_2$-C$_6$H$_3$– | 28 (20.1–38.9) | 278 | 9.93 |
| 18 | 2,4,6-(CH$_3$)$_3$-C$_6$H$_2$– | 34 (19.4–59.5) | 309 | 9.09 |

The compounds of this invention are used as a therapeutic agent for arrhythmia in the form of free base or in a form of pharmacologically acceptable salt, for instance, hydrochloride, which can be administered orally or non-orally singly or together with conventional harmless excipients in a suitable composition form such as capsule, tablet or injection. These compositions can be prepared by, for example, the following processes:

The active component is finely pulverized, which is mixed with a suitable excipient e.g. lactose, starch or a derivative thereof or a cellulose derivative, followed by a packing thus, mixed material into gelatin capsules; for preparing tablets, the active component is kneaded with, in addition to an excipient as above, a binder e.g. sodium carboxymethyl cellulose, alginic acid or gum arabica, and water, then the thus kneaded material is granulated by means of an extruder, followed by adding thereto a lubricant such as talc or stearic acid, which is tabletted by means of a conventional compression tabletting machine; for preparing injectable preparations, a water-soluble salt of a compound of this invention is dissolved in sterilized distilled water or sterilized physiological saline, which is ampouled with or without a suitable stabilizing agent and/or a suitable buffering agent.

Effective dose of an antiarrhythmic agent varies depending on administration method, types and degrees of arrhythmic and physical conditions of patients, but, in general, it should be an amount sufficient for causing dysrhythmia to normalize. In the case of a compound of this invention, a practical dosage is, when administered orally, 50–200 mg/day/adult, and this dosage is divided into 3–4 times, and, when administered by intravenous drip injection, 0.5–5 mg/kg (body weight) is used.

EXAMPLE

General Production Method 1.5–2 Equivalent each of various substituted aniline derivatives is dissolved in dioxane. To the solution is added 1.5–2 equivalent of sodium hydride while stirring at room temperature under nitrogen stream. The mixture is heated at 100° C. for two hours, then cooled to room temperature, followed by adding thereto dropwise a solution of one equivalent of 8-ethoxycarbonylmethyl pyrrolizidine dissolved in dioxane. Then, the mixture is again heated at 100° C. for two hours, and the reaction mixture is cooled. Under ice-cooling, ice and ether are added thereto. The mixture is subjected to extraction with 5% hydrochloric acid. The resulting hydrochloric acid layer is neutralized with sodium hydrogen carbonate, followed by washing with ether. The remaining aqueous layer is made alkaline with a 20% aqueous solution of sodium hydroxide, followed by extraction with chloroform. Thus-obtained chloroform layer is washed with saturated saline, then dried on magnesium sulfate, followed by removing the solvent under reduced pressure. The residue is made into its hydrochloride in accordance with a conventional manner, which is recrystallized from ethanol-ether. In accordance with the above-mentioned general method, by employing, as sustituted aniline derivatives, 2-methylaniline, 4-methylaniline, 2-chloroaniline, 2-bromoaniline, 2-methoxyaniline, 3-methoxyaniline, 4-methoxyaniline, 2-aminoaniline, 2,3-dimethylaniline 2,4-dimethylaniline, 2,5-dimethylaniline, 2,6-dimethylaniline, 3,4-dimethylaniline, 3,5-dimethylaniline, 2,5-dimethoxyaniline, 2,6-dichloroaniline, 2,6-diethylaniline, and 2,4,6-trimethylaniline, the respectively corresponding
N-(2-methylphenyl)-8-pyrrolizidineacetamide,
N-(4-methylphenyl)-8-pyrrolizidineacetamide,
N-(2-chlorophenyl)-8-pyrrolizidineacetamide,
N-(2-bromophenyl)-8-pyrrolizidineacetamide,
N-(2-methoxyphynyl)-8-pyrrolizidineacetamide,
N-(3-methoxyphenyl)-8-pyrrolizidineacetamide,
N-(4-methoxyphenyl)-8-pyrrolizidineacetamide,
N-(2-aminophenyl)-8-pyrrolizidineacetamide,
N-(2,3-dimetylphenyl)-8-pyrrolizidineacetamide,
N-(2,4-dimethylphenyl)-8-pyrrolizidineacetamide,
N-(2,5-dimethylphenyl)-8-pyrrolizidineacetamide,
N-(2,6-dimethylphenyl)-8-pyrrolizidineacetaminde,
N-(3,4-dimethylphenyl)-8-pyrrolizidineacetamide,
N-(3,5-dimethylphenyl)-8-pyrrolizidineacetamide,
N-(2,5-dimethoxyphenyl)-8-pyrrolizidineacetamide,
N-(2,6-dichlorophenyl)-8-pyrrolizidineacetamide,
N-(2,6-diethylphenyl)-8-pyrrolizidineacetamide, and
N-(2,4,6-trimethylphenyl)-8-pyrrolizidineacetamide
were prepared.

The physico-chemical properties of thus-obtained 8-substituted pyrrolizidine are shown by Table 2 in the order as above.

TABLE (II)

| Compound No. | R | m.p. (°C.) | Yield (%) | KBr method IR$\nu_{cm^{-1}}^{max}$ | NMR (free base, CDCl$_3$)δ | Elemental analysis (%) Theor. value | Exp. value |
|---|---|---|---|---|---|---|---|
| 1 | 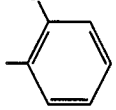 | 179–181 | 63.2 | 1675 (—CONH—) | 2.25 (3H, s, CH$_3$) 2.46 (2H, s, —CH$_2$CO—) 6.95–7.25 (3H, m, arom. proton) 8.15 (1H, dd, J=8 and 2Hz arom. proton) | C$_{16}$H$_{25}$ClN$_2$O C 65.18 H 7.86 N 9.50 | 65.10 7.83 9.35 |
| 2 | 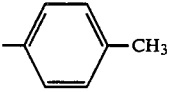 | 222–227 | 74.4 | 1680 (—CONH—) | 2.25 (3H, s, —CH$_3$) 2.38 (2H, s, —CH$_2$CO—) 7.70 (2H, d, J=8Hz, arom. proton) 7.42 (2H, d, J=8Hz, arom. proton) | C$_{16}$H$_{23}$ClN$_2$O C 65.18 H 7.86 N 9.50 | 65.03 7.90 9.76 |
| 3 | 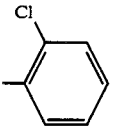 | 222–224 | 79.8 | 1685 (—CONH—) | 2.48 (2H, s, —CH$_2$CO—) 6.90–7.40 (3H, m, arom. proton) 8.50Hz (1H, dd, J=8 and 2Hz, 6' position H) | C$_{15}$H$_{20}$Cl$_2$N$_2$O C 57.15 H 6.40 N 8.89 | 57.07 6.52 8.90 |

TABLE (II)-continued

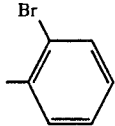

| Compound No. | R | m.p. (°C.) | Yield (%) | KBr method IR$\nu^{max}_{cm^{-1}}$ | NMR (free base, CDCl$_3$)δ | Elemental analysis (%) Theor. value | Exp. value |
|---|---|---|---|---|---|---|---|
| 4 | 2-Br-phenyl | 237–239 | 64.0 | 1680 (—CONH—) | 2.46 (2H, s, —CH$_2$CO—) 6.83–7.59 (3H, m, arom. proton) 8.49 (1H, dd, J=8 and 2Hz, 6' position H) | C$_{15}$H$_{20}$BrClN$_2$O C 50.08 H 5.60 N 7.79 | 50.11 5.61 7.71 |
| 5 | 2-CH$_3$O-phenyl | 189–196 | 51.6 | 1665 (—CONH—) | 2.45 (2H, s, —CH$_2$CO—) 3.85 (3H, s, —OCH$_3$) 6.78–7.04 (3H, m, arom. proton) 8.29–8.50 (1H, m, 6' position H) | C$_{16}$H$_{23}$ClN$_2$O$_2$ C 61.82 H 7.46 N 9.01 | 61.79 7.46 9.04 |
| 6 | 3-OCH$_3$-phenyl | 143.5–145 | 79.0 | 1675 (CONH)— | 2.42 (2H, s, —CH$_2$CO—) 3.80 (3H, s, —OCH$_3$) 6.48–7.40 (4H, m, arom. proton) | C$_{16}$H$_{23}$ClN$_2$O$_2$ C 61.82 H 7.46 N 9.01 | 61.73 7.52 9.21 |
| 7 | 4-OCH$_3$-phenyl | 201–204 | 72.7 | 1685 (—CONH—) | 2.41 (2H, s, —CH$_2$CO—) 3.72 (3H, s, —OCH$_3$) 6.80 (2H, d, J=9Hz, arom. proton) 7.44 (2H, d, J=9Hz, arom. proton) | C$_{16}$H$_{23}$ClN$_2$O$_2$ C 61.82 H 7.46 N 9.01 | 61.79 7.55 9.19 |
| 8 | 2-H$_2$N-phenyl | Picrate 191.5–196 | 43.8 | Picrate 1680 (—CONH—) | 2.47 (2H, s, —CH$_2$CO—) 6.61–7.12 (4H, m, arom. proton) | C$_{27}$H$_{27}$N$_9$O$_{15}$ C 45.19 H 3.79 N 17.57 | 45.19 3.80 17.30 |
| 9 | 2,3-(CH$_3$)$_2$-phenyl | 210–215 | 39.5 | 1675 (—CONH—) | 2.18 (3H, s, —CH$_3$) 2.29 (3H, s, CH$_3$) 2.49 (2H, s, CH$_2$CO—) 6.84–7.10 (2H, m, arom. proton), 7.87 (1H, dd, J=8 and 2Hz, 6' position H) | C$_{17}$H$_{25}$ClN$_2$O C 66.11 H 8.16 N 9.07 | 65.87 8.20 9.12 |
| 10 | 2,4-(CH$_3$)$_2$-phenyl | 173–175 | 40.2 | 1675 (—CONH—) | 2.22 (3H, s, —CH$_3$) 2.25 (3H, s, —CH$_3$) 2.44 (2H, s, —CH$_2$CO—) 6.87–7.10 (2H, m, arom. proton) 8.00 (1H, d, J=9Hz, 6' position H) | C$_{17}$H$_{25}$ClN$_2$O C 66.11 H 8.16 N 9.07 | 66.10 8.20 9.09 |
| 11 | 2,5-(CH$_3$)$_2$-phenyl | 211–212 | 57.5 | 1680 (—CONH—) | 2.22 (3H, s, —CH$_3$) 2.30 (3H, s, —CH$_3$) 2.46 (2H, s, —CH$_2$CO—) 6.75 (1H, dd, J=8 and 2 Hz, 4' position H) 7.02 (1H, d, J=8Hz, 3' position H) 8.01 (1H, d, J=2Hz, 6' position H) | C$_{17}$H$_{25}$ClN$_2$O C 66.11 H 8.16 N 9.07 | 66.27 8.27 9.23 |

TABLE (II)-continued

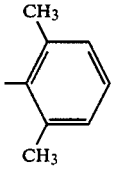

| Compound No. | R | m.p. (°C.) | Yield (%) | KBr method IR$\nu_{cm^{-1}}^{max}$ | NMR (free base, CDCl$_3$)δ | Elemental analysis (%) Theor. value | Exp. value |
|---|---|---|---|---|---|---|---|
| 12 | 2,6-dimethylphenyl (CH$_3$, CH$_3$) | 212–214 | 52 | 1665 (—CONH—) | 2.17 (6H, s, 2 × CH$_3$) 2.43 (2H, s, —CH$_2$CO—) 6.97 (3H, s, arom. proton) | C$_{17}$H$_{25}$ClN$_2$O C 66.11 H 8.61 N 9.07 | 66.03 8.26 9.01 |
| 13 | 2,3-dimethylphenyl (CH$_3$, CH$_3$) | 207–209.5 | 48.9 | 1675 (—CONH—) | 2.21 (3H, s, —CH$_3$) 2.26 (3H, s, —CH$_3$) 2.42 (2H, s, —CH$_2$CO—) 6.92–7.38 (3H, m, arom. proton) | C$_{17}$H$_{25}$ClN$_2$O C 66.11 H 8.16 N 9.07 | 66.25 8.14 9.08 |
| 14 | 2,5-dimethylphenyl (CH$_3$, CH$_3$) | 214–216 | 40.6 | 1685 (—CONH—) | 2.29 (6H, s, —CH$_3$) 2.42 (2H, s, —CH$_2$CO—) 6.68 (1H, Br.s, 4' position H) 7.16 (2H, Br.s, 2', 6' position H) | C$_{17}$H$_{25}$ClN$_2$O C 66.11 H 8.16 N 9.07 | 66.05 8.13 9.06 |
| 15 | 2,4-dimethoxyphenyl (CH$_3$O, OCH$_3$) | 73–77 | 41.6 | 1680 (—CONH—) | 2.45 (2H, s, —CH$_2$CO—) 3.77 (3H, s, —OCH$_3$) 3.82 (3H, s, —OCH$_3$) 6.48 (1H, dd, J=8 and 2 Hz, 4' position H) 6.79 (1H, d, J=8Hz, 3' position H) 8.18 (1H, d, J=2Hz, 6' position H) | C$_{17}$H$_{25}$ClN$_2$O$_3$·H$_2$O C 56.89 H 7.58 N 7.81 | 56.62 7.63 7.71 |
| 16 | 2,6-dichlorophenyl (Cl, Cl) | 229–231 | 56.6 | 1680 (—CONH—) | 2.54 (2H, s, —CH$_2$CO—) 7.05–7.40 (3H, m, arom. proton) | C$_{15}$H$_{19}$Cl$_3$N$_2$O C 51.52 H 5.48 N 8.01 | 51.26 5.49 8.09 |
| 17 | 2,6-diethylphenyl (C$_2$H$_5$, C$_2$H$_5$) | 217–218 (decomp.) | 61.1 | 1680 (—CONH—) | 1.18 (6H, t, J=7Hz, —CH$_2$CH$_3$) 2.50 (2H, s, —CH$_2$CO—) 2.57 (4H, q, —CH$_2$CH$_3$) 7.12 (3H, s, arom. proton) | C$_{19}$H$_{29}$ClN$_2$O C 67.73 H 8.68 N 8.32 | 67.65 8.72 8.61 |
| 18 | 2,4,6-trimethylphenyl (CH$_3$, CH$_3$, CH$_3$) | 226–228 | 49 | 1675 (—CONH—) | 2.17 (6H, s, 2 × CH$_3$) 2.22 (3H, s, CH$_3$) 2.47 (2H, s, —CH$_2$CO—) 6.83 (2H, s, arom. proton) | C$_{18}$H$_{27}$ClN$_2$O C 66.96 H 8.43 N 8.68 | 66.79 8.46 8.67 |

We claim:
1. An 8-substituted pyrrolizidine compound of the formula:

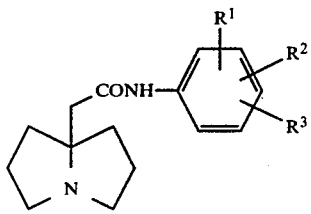

wherein $R^1$ stands for hydrogen or a lower alkyl group, $R^2$ stands for hydrogen, a lower alkyl group, a lower alkoxy group or halogen, and $R^3$ stands for a lower alkyl group, a lower alkoxy group, amino group or halogen.

2. A compound as claimed in claim 1, wherein $R^1$ and $R^2$ both stand for hydrogen, and $R^3$ stands for methyl group, methoxy group, amino group, chlorine or bromine.

3. A compound as claimed in claim 1, wherein $R^1$ stands for hydrogen, and $R^2$ and $R^3$ respectively stand for methyl group, ethyl group, methoxy group or chlorine.

4. A compound as claimed in claim 1, wherein $R^1$, $R^2$ and $R^3$ respectively stand for methyl group.

5. A compound as claimed in claim 1, which is selected from the group consisting of N-(2-methylphenyl)-8-pyrrolizidineacetamide, N-(4-methyphenyl)-8-pyrrolizidineacetamide, N-(2-chlorophenyl)-8-pyrrolizidineacetamide, N-(2-bromophenyl)-8-pyrrolizidineacetamide, N-(2-methoxyphenyl)-8-pyrrolizidineacetamide, N-(3-methoxyphenyl)-8-pyrrolizidineacetamide, N-(4-methoxyphenyl)-8-pyrrolizidineacetamide, N-(2-aminophenyl)-8-pyrrolizidineacetamide, N-(2,3-dimethylphenyl)-8-pyrrolizidineacetamide, N-(2,4-dimethylphenyl)-8-pyrrolizidineacetamide, N-(2,5-dimethylphenyl)-8-pyrrolizdineacetamide, N-(2,6-dimethylphenyl)-8-pyrrolizidineacetamide, N-(3,4-dimethylphenyl)-8-pyrrolizidineacetamide, N-(3,5-dimethylphenyl)-8-pyrrolizidineacetamide, N-(2,5-dimethoxyphenyl)-8-pyrrolizidineacetamide, N-(2,6-dichlorophenyl)-8-pyrrolizidineacetamide, N-(2,6-diethylphenyl)-8-pyrrolizidineacetamide, and N-(2,4,6-trimethylphenyl)-8-pyrrolizidineacetamide.

6. An antiarrhythmic composition comprising a pharmaceutically acceptable carrier and a pharmaceutically effective amount of an 8-substituted pyrrolizidine compound of the formula:

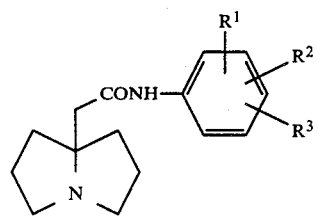

wherein $R^1$ is hydrogen or a lower alkyl group, $R^2$ is hydrogen, a lower alkyl group, a lower alkoxy group or halogen, and $R^3$ is a lower alkyl group, a lower alkoxy group, amino group or halogen.

7. A method for the treatment of arrhythmia which comprises administering a pharmaceutically effective amount of the composition of claim 6.

8. The method of claim 7 wherein said pharmaceutically effective amount is 50 to 500 milligrams per day.

* * * * *